US006338841B1

(12) United States Patent
Mattai et al.

(10) Patent No.: US 6,338,841 B1
(45) Date of Patent: Jan. 15, 2002

(54) ANTIPERSPIRANT PRODUCT WITH DIBENZYLIDENE SORBITOL AND ELASTOMER IN DIMETHICONE

(75) Inventors: Jairajh Mattai, Piscataway; Claudio Ortiz, Dayton; Eric Guenin, Pennington; John Afflitto, Brookside, all of NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/682,101

(22) Filed: Jul. 19, 2001

(51) Int. Cl.[7] .............................. A61K 7/32; A61K 7/34; A61K 7/36; A61K 7/38; A61K 7/00
(52) U.S. Cl. .......................... 424/65; 424/66; 424/67; 424/68; 424/400; 424/401
(58) Field of Search ............................. 424/65, 66, 67, 424/68, 400, 401

(56) References Cited

U.S. PATENT DOCUMENTS

| | | |
|---|---|---|
| 4,346,097 A | 8/1982 | Schweiss et al. |
| 4,440,742 A | 4/1984 | Marschner |
| 4,518,582 A | 5/1985 | Schamper et al. |
| 4,719,102 A | 1/1988 | Randhawa et al. |
| 4,720,381 A | 1/1988 | Schamper et al. |
| 4,722,835 A | 2/1988 | Schamper et al. |
| 4,725,430 A | 2/1988 | Schamper et al. |
| 4,816,261 A | 3/1989 | Luebbe et al. |
| 4,822,602 A | 4/1989 | Sabatelli |
| 4,863,721 A | 9/1989 | Beck et al. |
| 5,302,382 A | 4/1994 | Kasprazak |
| 5,405,605 A | 4/1995 | Shin |
| 5,449,519 A | 9/1995 | Wolf et al. |
| 5,463,098 A | 10/1995 | Giovanniello et al. |
| 5,490,979 A | 2/1996 | Kasat et al. |
| 5,500,209 A | 3/1996 | Ross et al. |
| 5,531,986 A | 7/1996 | Shevade et al. |
| 5,603,925 A | 2/1997 | Ross et al. |
| 5,609,855 A | 3/1997 | Oh et al. |
| 5,725,846 A | 3/1998 | Vu et al. |
| 5,871,720 A | 2/1999 | Gutierrez et al. |
| 5,895,644 A | 4/1999 | Albanese et al. |
| 5,925,338 A | 7/1999 | Karassik et a. |
| 6,171,581 B1 | 1/2001 | Joshi et al. |
| 6,180,125 B1 | 1/2001 | Ortiz et al. |

FOREIGN PATENT DOCUMENTS

| | | |
|---|---|---|
| EP | 0260030 | 8/1987 |
| EP | 0291334 | 5/1988 |
| GB | 2280111 | 1/1995 |
| WO | WO9219221 | 11/1992 |
| WO | WO9626709 | 9/1996 |
| WO | WO0128510 | 4/2001 |

OTHER PUBLICATIONS

"Novel Formulations Based on Nonaqueous Emulsions of Polyols in Siicones" Presented at the 19th IFSCC Congress, Sydney Australia, on Oct. 22–25, 1996, by A. Zombeck, Dow Corning Corporation.

"Acid Stable Dibenzylidene Sorbitol Gelled Clear Antiperspirant Systems", Journal Soc. Cosmetic Chemicals, vol. 37, pp. 225–231; (Jul./Aug. 1986).

Book: "Transdermal Control of System Medications" edited by Yie Chien. vol. 31, 1987.

*Primary Examiner*—Shelley A. Dodson
(74) *Attorney, Agent, or Firm*—Rosemary M. Miano

(57) ABSTRACT

This invention comprises a clear to translucent anhydrous stick or gel antiperspirant and/or deodorant product having low tack and comprising: (a) a solvent phase comprising: (i) 0.2–4.0 weight % dibenzylidene sorbitol; (ii) 0.05–1.0 weight % of a co-gellant or structural integrity enhancer; (iii) 25–75 weight % of a solvent selected from the group consisting of polyhydric alcohols; (iv) an effective amount of an antiperspirant or deodorant; and (v) 0.1–5 weight % dimethicone copolyol; and (b) an oil phase comprising: (i) 0.25–5 weight % of a silicone elastomer (on a solids basis) in a first dimethicone wherein the dimethicone has a viscosity in the range of 6–100 centistokes and a flashpoint in the range of about greater than 115 degrees C. to 300 degrees C.; and (ii) 1–25 weight % of a second dimethicone (including the dimethicone from part (b)(i)), wherein the second dimethicone may be selected from the same group or a different group than the first dimethicone; and (iii) 0–10 weight % emollients; wherein the oil phase is 5–50% of the composition and the solvent phase is 50–95% of the composition.

13 Claims, No Drawings

ANTIPERSPIRANT PRODUCT WITH DIBENZYLIDENE SORBITOL AND ELASTOMER IN DIMETHICONE

BACKGROUND OF INVENTION

This invention relates to cosmetic compositions in the form of solid sticks or gels, which are based on emulsions comprising a gellant/solvent phase gelled with dibenzylidene sorbitol (DBS) and an oil phase wherein the oil phase is made with a silicone elastomer in a selected dimethicone. The use of an elastomer in this selected dimethicone with a DBS formulation results in antiperspirant and/or deodorant products with improved aesthetics and efficacy.

Dibenzylidene sorbitol (also called dibenzaldehyde monosorbitol acetal, or dibenzyl monosorbitol acetal or dibenzylidene monosorbitol acetal) and derivatives thereof such as those which are substituted on one or both of the aromatic rings with a fluorine or methoxy group and those which have the sorbitol portion replaced with other reduced sugars such as xylitol or ribitol as described in U.S. Pat. No. 5,609,855 assigned to Procter & Gamble (collectively referred to as dibenzylidene sorbitol or DBS) may be used in various food and cosmetic applications. For cosmetic uses the more interesting ones are those focused on obtaining a translucent or clear product. While dibenzylidene sorbitol is stable in alkaline or neutral media, such compounds are not stable in acidic media. In an acidic environment, such as in the presence of acidic antiperspirant materials, and in the presence of even small amounts of water, the dibenzylidene sorbitol deteriorates and breaks down. Also, the use of DBS sometimes causes problems in the aesthetics of cosmetic products or problems with structural properties. Accordingly, there is a need to find a way to form products containing DBS which are stable and which have acceptable aesthetics.

The use of DBS in an antiperspirant formulation requires the inclusion of polyhydric alcohols such aspropylene glycol as a solvent if a clear, transparent product is desired. The high propylene glycol content, when combined with aluminum salts which are included in antiperspirant compositions for wetness control, contribute to undesirable tackiness or a sticky feel for these products when applied to the axilla region of the body. Clear antiperspirant sticks were first formulated with DBS in the late 1970's. Since then there have been continued technical efforts to reduce the negative sensory attributes. Some of these efforts have focused on alternative solvents to replace a portion of the propylene glycol with organic esters known in the art as emollients. This creates a further problem since many of these emollients are either unsafe for personal care products or do not achieve acceptable aesthetics.

For formulating personal care products the incorporation of silicone fluids is known in the art. Silicone fluids such as cyclosiloxanes (for example, DOW CORNING® 244 and 245 Fluids) are used in some major commercial products. Silicone fluids are used because of their low tackiness, superior glide and skin-feel properties. However, silicone fluids are difficult to introduce into DBS based cosmetic stick products such as antiperspirants because they are not good solvents for DBS and they are not readily compatible with propylene glycol and many organic esters or emollients. One example of DBS based formulations is WO 01/2851 0 assigned to Unilever. This document describes the use of a broadly defined (and nontraditional) version of "dimethicone" as being useful in such DBS formulations.

Some of the efforts to overcome these problems are described as follows. For example, some efforts have focused on the stability of DBS. United Kingdom Patent GB 2 280 111 assigned to Union Camp Corporation, describes a gel stick composition comprising a dihydric alcohol as a primary solvent, a co-solvent such as low molecular weight polyethylene glycol, water and/or glycerine, a buffering agent and DBS as a gelling agent.

U.S. Pat. No. 4,720,381 to Schamper et al notes stability problems with this approach and itself describes the use of solvents having less reactive hydroxy groups or alcohols with selected chain lengths in a DBS composition.

U.S. Pat. No. 4,816,261 to Luebbe et al describes stable deodorant gel stick compositions comprising DBS with a polar solvent and a coupling agent such as polypropylene glycol ethers of fatty alcohols.

U.S. Pat. No. 4,822,602 to Sabatelli teaches the use of dimethicone copolyols and volatile silicones in clear DBS-based sticks.

U.S. Pat. No. 5,405,605 to Shin teaches anhydrous clear antiperspirant sticks substantially free of lower monohydroxy alcohols which sticks contain dibenzylidene monosorbitol with weak basic organic nitrogen containing compounds as a stabilizing agent.

U.S. Pat. No. 4,518,582 to Schamper et al discloses an antiperspirant stick composition containing dibenzyl monosorbitol acetal in the presence of acidic antiperspirant-active salts, which composition is stable for extended periods of time at elevated temperatures. The composition contains at least a reactive solvent (such as water, methanol, ethanol, n-propanol, ethylene glycol, 1,2-propylene glycol, 1,3-propylene glycol, etc.), dibenzyl monosorbitol acetal, an antiperspirant-active compound, and a gel stabilizer such as magnesium sulfate, zinc acetate and mixtures thereof. This patent discloses that the stabilizer prevents or retards deterioration of the gelled sticks, especially when exposed to elevated temperatures.

Another patent disclosing stabilizers for solid gel antiperspirant sticks containing an acidic antiperspirant-active compound in the presence of dibenzyl monosorbitol acetal is U.S. Pat. No. 4,719,102 to Randhawa et al. This patent discloses that the sticks include a solvent which is a small, polar organic compound such as cyclic esters, amides, amines, ketones, ureas, carbamates, sulfoxides and sulfones, and their open chain analogs; a cosolvent such as primary or low molecular weight alcohols and/or glycols; dibenzyl monosorbitol acetal; an antiperspirant-active compound; and a gel stabilizer such as N-(2-hydroxyethyl) fatty ($C_8$–$C_{20}$) acid amides, magnesium sulfate, zinc acetate, acetamide monoethanol amine and hexamethylenetetramine, and mixtures thereof.

U.S. Pat. No. 4,722,835 to Schamper et al also discloses antiperspirant gel stick compositions gelled with dibenzyl monosorbitol acetal and containing an acidic antiperspirant compound as well as a stabilizer for the gel. This patent teaches that the compositions include a solvent which is a small, polar organic compound, as discussed previously in connection with U.S. Pat. No. 4,719,102; dibenzyl monosorbitol acetal; an antiperspirant-active compound; and a gel stabilizer such as zinc oxide, calcium acetate, magnesium oxide, calcium carbonate, calcium hydroxide, magnesium carbonate, sodium carbonate, zinc carbonate and potassium carbonate. The basic metallic salt gel stabilizers are said to stabilize the gel, even at high temperatures.

U.S. Pat. No. 5,490,979 to Kasat et al describes a clear DBS stick comprising guanidine carbonate as the buffer and which is made by a unique processing method.

Other patent documents also disclose antiperspirant sticks gelled with dibenzylidene sorbitol and include stabilizers for the gel.

EP Application No. 451 002 A2 discloses a stable, substantially anhydrous and substantially lower monohydric alcohol free, transparent, gelled, antiperspirant composition gelled by dibenzylidene monosorbitol acetal, containing acidic antiperspirants, and utilizing dihydric alcohols containing 3 to 6 carbon atoms as solvents, with the acetal being stabilized against hydrolysis and the formation of benzaldehyde by the presence of a stabilizing amount of a selected organic base, the organic base being a weakly basic, nitrogen-containing, organic compound.

EP Application No. 512 770 A1 discloses a stable, substantially anhydrous and substantially lower aliphatic monohydroxy alcohol free cosmetic composition gelled by dibenzylidene monosorbitol acetal, and containing acidic antiperspirant compounds and utilizing dihydroxy aliphatic alcohols containing 3–6 carbon atoms as solvents, wherein the dibenzylidene monosorbitol acetal gelling agent is stabilized against hydrolysis and the formation of benzaldehyde by the presence of a stabilizing amount of a selected inorganic base, the inorganic base including alkali and alkaline earth metal oxides, hydroxides, carbonates or bicarbonates, and trivalent metallic hydroxides.

PCT No. WO 92/19221 discloses solid antiperspirant compositions in gel stick form, having an acid pH, and including (1) an antiperspirant active; (2) a gelling agent selected from the group consisting of substituted and unsubstituted dibenzylidene alditols; (3) a solvent for the gelling agent, preferably including a solvent material selected from the group consisting of monohydric and polyhydric alcohols, and mixtures thereof; and (4) a gelling agent stabilizer, the stabilizer being a basic metallic salt of an acid having a pKa of from about 3.8 to about 6.5 at 25 degrees C., the salt being at least partially soluble in the composition and being selected from the group consisting of $C_4$–$C_6$ dicarboxylate salts, $C_6$–$C_8$ monocarboxylate salts, and substituted or unsubstituted benzoate salts, and mixtures thereof, the gelling agent stabilizer not containing amino or amido functionalities. It is stated that for clear or translucent sticks, the gelling agent stabilizer present in the composition should be fully soluble in the composition, in order to minimize refraction of light.

Further references of interest include U.S. Pat. No. 6,171,581 to Joshi et al describing a water and oil emulsion made with a silicone elastomer and U.S. Pat. No. 5,925,338 to Karassik et al describing clear antiperspirant or deodorant gel compositions made with volatile linear silicone such as a dimethicone to reduce staining while retaining good aesthetics and efficacy.

The foregoing patent documents also disclose methods for forming the disclosed antiperspirant stick compositions containing the antiperspirant materials and gelling agent. Attention is directed to U.S. Pat. No. 4,719,102 and U.S. Pat. No. 4,722,835. Each of these patents discloses processes of forming the stick compositions, including dissolving the antiperspirant active in one phase and the dibenzyl monosorbitol acetal gellant in another phase. The two phases are then combined and poured into a mold or into the final package. The other components are added to either of the two phases depending on the compatibility of the component with the phases. More phases can be utilized, if desired, by forming a separate solution of some of the components, with the separate phases then being added to either of the two main phases; or all of the phases could be poured together at the end, as, for example, with a multi-stream filling head or an in-line mixer.

There have also been efforts to develop DBS compositions to improve the aesthetics and/or mechanical properties while not sacrificing stability.

U.S. Pat. No. 4,346,097 to Roehl discloses a solid translucent gelled antiperspirant composition comprising DBS with an oleaginous compound (such as selected siloxanes, selected esters with an aliphatic character and branched chain hydrocarbons) to reduce stickiness.

U.S. Pat. No. 5,725,846 to Vu et al describes a clear gel cosmetic stick which includes a liquid vehicle, an antiperspirant salt dissolved in the liquid vehicle, DBS and one or both of hydroxypropyl cellulose and a chelating agent. The hydroxypropyl cellulose maintains the hardness of the stick.

U.S. Pat. No. 5,895,644 to Albanese et al describes a clear gel cosmetic stick which includes a liquid vehicle, an antiperspirant salt dissolved in the liquid vehicle, DBS and the use of selected guars.

U.S. Pat. No. 4,863,721 to Beck et al describes the use of particulate cellulose ether polymers such as hydroxyethyl cellulose in antiperspirant compositions which are substantially free of polar solvents.

European Pat. No. 0 260 030 B1 assigned to Unilever N.V. describes a transparent deodorant stick containing DBS and a thickening agent such as a chemically modified cellulose, polyacrylic acid, and/or polyacrylic acid copolymers and mixtures of the foregoing.

Other references of interest include U.S. Pat. No. 4,472,835 to Schamper et al; Zombeck, A., "Novel Formulations Based on Nonaqueous Emulsions of Polyols in Silicones" (Paper presented at the $19^{th}$ IFSCC Congress, Sydney, Oct. 22–25, 1996); and Schamper, T., et al, "Acid Stable Dibenzylidene Sorbitol Gelled Clear Antiperspirant Systems", *J. Soc. Cosmet. Chem.*, Vol. 37, pages 225–231 (July/August 1986); Smith, J. M., et al, *J. Mater. Chem.*, 5(11): 1899–1903 (1995).

There continues to be efforts to formulate improved cosmetic compositions especially sticks which have translucent to clear appearance and which have aesthetically acceptable properties. U.S. Pat. No. 5,500,209 to Ross et al describes a gel or stick composition for reduction of body malodor using a polyamide gelling agent. This composition is stated to have good stability and to be able to provide a clear antiperspirant or deodorant product with good structural integrity.

U.S. Pat. No. 5,603,925 to Ross et al teaches the use of a polyamide gelling agent in an antiperspirant product. The composition uses a glycol-free solvent system to reduce the problems of tack and achieve more acceptable properties.

U.S. Pat. No. 4,440,742 to Marchner discloses a stable cosmetic stick deodorant without the use of bacteriostats and comprising a polyhydric alcohol (such as propylene glycol) solidified by a fatty acid soap and containing from 0.1–70% alkali metal bicarbonate.

U.S. Pat. No. 4,822,602 to Sabatelli describes cosmetic compositions such as deodorant and antiperspirant sticks comprising (a) water-soluble active; (b) dimethicone copolyol; (c) volatile silicone oil; (d) propylene glycol; (e) C2–C4 monohydric alcohol; (f) water; (g) solidifying agent (such as soap type gel forming agents and DBS); and (h) coupling agent (such as C6–C22 fatty alcohols and propylene glycol ethers of C4–C22 fatty alcohols).

U.S. Pat. No. 4,725,430 teaches a clear or translucent cosmetic stick containing an acidic material (such as antiperspirant salts) and a reactive solvent (for example, various propylene glycols) using DBS as the gelling agent and an N-(2-hydroxyethyl)acetamide as the stabilizing agent.

U.S. Pat. No. 5,302,382 to Kasprzak describes a method of making stable emulsified personal care products which includes the steps of (i) forming an anhydrous silicone mixture having a silicone oil or silicone gum with two silicone oxyalkylene copolymers; (ii) forming an aqueous based pre-emulsified personal care product; and (iii) adding the anhydrous silicone mixture directly to the pre-emulsified personal care product without further emulsification.

U.S. Pat. No. 5,449,519 to Wolf et al describes a cosmetically acceptable composition with keratolytic activity which composition includes a carrier molecule having at least one hydroxyl or amino group.

U.S. Pat. No. 5,531,986 to Shevade et al describes a low residue antiperspirant solid stick containing an antiperspirant active, volatile and nonvolatile silicone materials, dimethicone copolyol and high-melting point and low-melting point waxes.

As described above, it is well known in the art that silicone containing compounds impart good aesthetic characteristics to personal care products. These characteristics include lubricity (glide), conditioning, dry feel and low tack. The addition of a silicone material to a DBS/PG formulation is not easy because of the insolubility of the usual silicone ingredients (for example, cyclomethicone or dimethicone) in propylene glycol.

A recent attempt to incorporate silicone has been published in U.S. Pat. No. 5,871,720 to Albanese et al, where a functionalized silicone was found to provide the good characteristics mentioned above. This technology involves two phases since the silanol used is not soluble in PG. Also, in order to be clear the two phases need to have the same or closely matched refractive indices (RI).

Another recent patent of interest is U.S. Pat. No. 6,180,125 to Ortiz et al, which includes the use of dimethicone copolyol ester in a one-phase stick gelled with DBS.

The use of DBS in antiperspirant formulations has been difficult. While the use of DBS as a gelling agent is helpful to clarity, there are significant problems with tack that result from the combination of ingredients used. In addition to overcoming the problems of tack, it is also desired to improve the efficacy of such products. Even in view of the art previously described, there still remains a need to develop cosmetic products made with DBS which are translucent (preferably clear), which provide reduced tack in the final cosmetic product while preserving efficacy. Thus, it is an object of the present invention to provide a cosmetic composition which comprises DBS and which provides reduced tack when applied to the skin. It is a further object of the invention to provide cosmetic compositions containing DBS which can be used to form deodorant and/or antiperspirants which are translucent to clear and which have good efficacy. These and other objects of the invention will be apparent from the following description of the invention.

SUMMARY OF THE INVENTION

This invention comprises a clear to translucent anhydrous stick or gel having low tack. These products are based on emulsions comprising a gellant/solvent phase gelled with dibenzylidene sorbitol (DBS) and an oil phase wherein the oil phase is made with a silicone elastomer in dimethicone, and the emulsions are formed by combining the components described below. In general, the oil phase (internal phase) is 5–50% of the composition and the gellant/solvent phase is 50–95% of the composition. These components are all listed in weight percent based on the total weight of the composition: (a) a solvent phase comprising: (i) 0.2–4.0 weight % dibenzylidene sorbitol (for example, 1.5–4.0% if a stick is made and 0.2–1% if a gel is made); (ii) 0.05–1.0 weight % of a co-gellant (the term co-gellant includes gelling agents as well as other structural integrity enhancers) which is selected from the group consisting of hydroxyethylcellulose, hydroxypropyl cellulose, methylcellulose, and hydroxypropylmethylcellulose, especially hydroxypropyl cellulose; (iii) 25–75 weight % of a solvent selected from the group consisting of polyhydric alcohols for example, propylene glycol, dipropylene glycol, tripropylene glycol and tetrapropylene glycol, PPG-10 butane diol, 1,3-butane diol, PEG-6, PPG-425, 2-methyl-1,3-propane diol ("MP Diol") and mixtures thereof, optionally including up to 50 percent of other solvents selected from the group consisting of propylene carbonate, diisopropyl sebacate, methyl pyrrolidone, and ethyl alcohol as a substitute for a portion of the polyhydric alcohol component; (iv) an effective amount of at an antiperspirant or deodorant (for example, 5–25 weight % on an actives basis of an aluminum zirconium salt stabilized with glycine (referred to in the art as a "ZAG", such as 17.8–71.4 weight % of a ZAG in propylene glycol as a 28% solution, or an equivalent amount using a different dilution); and (v) 0.1–5 weight % dimethicone copolyol; and (b) an oil phase comprising: (i) 0.25–5 weight % of a silicone elastomer (on a solids basis) in a first dimethicone (for example, 1–20% elastomer in dimethicone at a concentration of 25% elastomer or its equivalent), wherein the dimethicone has a viscosity in the range of 6–100 centistokes (particularly 6–50 centistokes, and especially about 6 centistokes) and a flashpoint in the range of about greater than 115 degrees C. to 300 degrees C. (with a particular example being KSG-16 silicone elastomer in 6 cst dimethicone from Shin-Etsu Silicones of America (Akron, Ohio)); (ii) 1–25 weight % of a second dimethicone (including the dimethicone from part (b)(i)) which may or may not be selected from the same group as the first dimethicone (preferably the second dimethicone is of the type described in part (b)(i) particularly having a viscosity in the range of 6–100 centistokes (such as 6–50 centistokes, and especially about 6 centistokes)). The compositions of this invention are anhydrous and will contain less than 5% water from all sources (including waters of hydration from the antiperspirant salt and water contaminants from the raw materials used); and (iii) 0–10 weight % of an emollient (for example, 0.1–10 weight % phenyl trimethicone).

While some elastomers come premixed with a solvent (for example, KSG-16 from Shin-Etsu), it is also possible to take a solid elastomer material such as JEESILC 35 C from Jeen International Corporation (Fairfield, N.J.) and mix it with a dimethicone of the type described above. It is also possible that any of the commercially available silicone elastomers currently offered in mixture with cyclomethicone could be made with one or more dimethicones instead of cyclomethicone (for example, KSG-15 from Shin-Etsu and DC-9040 from Dow Corning).

Optionally one or more members selected from the group consisting of at least one additional member selected from the group consisting of emollients, fragrances, coloring agents, etc. may be added. If fragrance is used, it is preferably added so as to minimize its evaporation and may be added to ether the oil or water phases depending on its solubility. The use of elastomers in the dimethicones provides the desired emolliency in this DBS system. While provision is made for the optional use of additional emollients (for example, phenyl trimethicone for refractive index matching), the use of additional emollients is not needed or desired, especially because of the detrimental effect on efficacy.

The compositions of this invention are made by combining the components described above to form a gelled composition which may be in the form of a stick or a gel. In accordance with the present invention sticks or gels can be made by combining the materials listed above using conventional mixing techniques.

DETAILED DESCRIPTION

The following and more particular description of the invention more fully explains the antiperspirant and/or deodorant compositions that can be made. An important feature of the invention is that the use of a silicone elastomer in a dimethicone results in a product that has reduced tack and improved efficacy.

The term "dimethicone" as used herein has the traditional meaning of a polydialkylsiloxane polymer such as polydimethylsiloxane polymer and does not include phenyl trimethicone, dimethicone copolyols, bis-phenylpropyl dimethicone or blended dimethicones that contain water. The term "first dimethicone" as used in this application with the elastomer component of part (b)(i) has the limitations described therein. Additionally, because of the chemistry definition and viscosity limitations of (b)(i), solids such as Dow Corning DC 2501 (which is also a copolyol) will be excluded from (b)(i). (Note that DC 2501 is a copolyol and is also excluded from the definition of dimethicone according to (b) (ii); however, it is listed herein as a possible emollient.) Because of the anhydrous nature of the formulations of the composition, the term dimethicone as used with all aspects of this invention (that is, both (b)(i) and (b)(ii) excludes blends of dimethicones with water (for example, AF9030 and AF9020 emulsion products from General Electric which contain 30–60% or 60–80% water, respectively, along with surfactant and silica). When phenyl trimethicone or other types of silicones that do not fall under the category of polydialkylsiloxane polymer are used, they will be described separately in the emollient category, below.

The hydroxypropyl cellulose that is preferred may be selected from the group consisting of hydroxypropyl cellulose of the brand designation KLUCELL MF from Hercules Inc. (Wilmington, Del.).

Various antiperspirant active materials that can be utilized according to the present invention include conventional aluminum and aluminum/zirconium salts, as well as aluminum/zirconium salts complexed with a neutral amino acid such as glycine, as known in the art. See each of EP Application No. 512 770 A1 and PCT No. WO 92/19221, the contents of each of which are incorporated herein by reference in their entirety, for disclosure of antiperspirant active materials. The antiperspirant active materials disclosed therein, including the acidic antiperspirant materials, can be incorporated in the compositions of the present invention. Suitable materials include (but are not limited to) aluminum chlorohydroxide, aluminum chloride, aluminum sesquichlorohydroxide, zirconyl hydroxychloride, and aluminum chlorohydrol-propylene glycol complex. These include, by way of example (and not of a limiting nature), aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex PG, aluminum chlorohydrex PEG, aluminum dichlorohydrex PG, and aluminum dichlorohydrex PEG.

The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as aluminum nitratohydrate and its combination with zirconyl hydroxychlorides and nitrates, or aluminum-stannous chlorohydrates, can be incorporated as an antiperspirant active ingredient in antiperspirant compositions according to the present invention. Preferred antiperspirant actives that can be incorporated in the compositions of the present invention include the enhanced efficacy aluminum salts and the enhanced efficacy zirconium/aluminum salt-glycine materials, having enhanced efficacy due to improved molecular distribution, known in the art and discussed, for example, in PCT No. WO 92/1 9221, the contents of which are incorporated by reference in their entirety herein.

A particular group of antiperspirant actives of interest include those selected from the group consisting of aluminum chlorohydrate, aluminum-zirconium glycine complex (for example, aluminum zirconium trichlorohydrex gly, aluminum zirconium pentachlorohydrex gly, aluminum zirconium tetrachlorohydrex gly), aluminum chlorohydrex PG, and aluminum chlorohydrex PEG.

Another particular group consists of aluminum zirconium salts stabilized with glycine or zinc glycinate.

The amount of antiperspirant active material incorporated in the stick composition of the present invention is, preferably, an antiperspirant effective amount; that is, an amount to reduce the flow of perspiration from the location (for example, axillary region of a human) to which the antiperspirant is applied. For deodorant products a level of from 0.5–20%, more particularly 0.5–5.0% by weight based on the entire weight of the composition is used. For an antiperspirant product an amount of 5.0–25%, particularly 5–20%, even more particularly 7–15% by weight based on the total weight of the composition may be used. The amount of antiperspirant material utilized is dependent on the efficacy of the specific antiperspirant material, as well as a maximum amount which avoids a reduction in clarity of the final product.

A separate category of antiperspirant actives include those which are more experimental in nature and not yet included in the aluminum containing materials listed above (both Monograph approved and non-Monograph approved). These are called low dose antiperspirant actives herein and may be substituted for the Monograph type antiperspirant actives, but in much lower amounts such as in the range of 0.0001–10%. These low dose antiperspirant actives may be selected from the group consisting of (a) 0.5–10% formaldehyde derivatives such as methenamine, methenamine mandelate and methenamine hippurate; and (b) 0.0001–1% (with higher amounts in the 0.5–1% range being dosed via time released mechanisms for safety reasons) of anticholinergics (for example, H1-histamine blockers). In antiperspirant compositions the methenamine derivatives degrade slowly to formaldehyde, but the level of formaldehyde never reaches a point of skin irritation. These methenamine derivatives can be added in amounts in the range of 0.5–10% by weight, based on the total weight of the composition. Another class of compounds are the anticholinergic compounds which act on the nervous system, specifically on the sympathetic cholinergic fibers of the eccrine sweat glands. Compounds such as H1-histamine blockers have an antiperspirant effect via an anticholinergic effect. Examples of suitable anticholinergic agents include methscopolamine bromide, scopolamine hydrobromide, and N-methyl-4-piperidinyl alpha-benzoyloxy-alpha-cyclopentylphenylacetate salts. The anticholinergics can be used in amounts in the range of 0.000–1% by weight based on the weight of the entire composition, with amounts in the 0.5–1% range being dosed via time released compositions for safety reasons. Such time released vehicles are described, for example, in "*Transdermal Control Systemic Medications*" by Yie W. Chien (Marcel Dekker Inc., New York, N.Y.).

For embodiments of the invention which contain an antiperspirant (either at a level denominated deodorant or at a level denominated antiperspirant) it is preferred that a stabilizing agent also be included. Examples of suitable stabilizing agents include cosmetically acceptable alkali metal salts, bases, amines and other nitrogen containing compounds, particularly zinc glycinate (described in U.S. Pat. No. 5,463,098).

Antimicrobials and bacteriostats may be used to impart deodorancy. Known antimicrobials and bacteriostats include bacteriostatic quaternary ammonium compounds such as 2-amino-2-methyl-1-propanol (AMP), cetyl-trimethylammonium bromide, cetyl pyridinium chloride, 2, 4, 4"-trichloro-2"-hydroxydiphenylether (Triclosan), N-(4-chlorophenyl)-N"-(3,4-dichlorophenyl)urea (Triclocarban) and various zinc salts (for example, zinc ricinoleate). The antimicrobial orbacteriostat can, illustratively, be included in the composition in an amount of 0.01–1.0% by weight,of the total weight of the composition. Triclosan, can illustratively be included in an amount of from 0.01% to about 0.5% by weight, of the total weight of the composition.

A critical part of the invention is the use of elastomers that do not contain appreciable amounts of cyclomethicone. While the use of silicone elastomers imparts good aesthetics to antiperspirant and/or deodorant products, it has been found that the use of cyclomethicones which are used as the vehicles for many elastomers causes problems in the processing of formulations containing DBS. It has been found that adding elastomers which are used in a mixture with a dimethicone having a viscosity in the range of 6–100 centistokes (1) allows for easier processing of DBS formulations because of the higher flashpoints of the selected dimethicones useful in this invention and (2) provides products that have improved efficacy because of the ability to use higher amounts of antiperspirant active in the formulations without affecting tackiness. The selected dimethicones described herein appear to be unique in the balance of flash point and volatility parameters. At this point other solvents for silicone elastomers have not been found that have this unique combination of properties. Thus, the use of silicone elastomers with dimethicone results in improved aesthetics and better efficacy.

With respect to the dimethicone component for both the elastomer and the overall composition, products with a methyl polysiloxane structure and a viscosity in the range of 6–100 centistokes, particularly 6–50 centistokes and especially about 6 centistokes may be used. Such dimethicones will have a refractive index in the range of about 1.397–1.403, and a flash point of about greater than 115 degrees C. to 300 degrees C. One particular elastomer of interest that comes mixed with an appropriate dimethicone is KSG-16 from Shin-Etsu Silicones of America (Akron, Ohio). KSG-16 is a dimethicone/vinyidimethicone crosspolymer composition made by reacting (in the presence of a platinum catalyst) a polymethylhydrogensiloxane with an alpha, omega-divinylpolydimethyl siloxane for which the dimethicone/vinyidimethicone crosspolymer composition (1) is used at a concentration of 20–30% in dimethicone of about 6 cst; and (2) has a refractive index of 1.390–1.410. Another elastomer that comes only as a solid (such as JEESILC 35C) will have to be mixed with a suitable dimethicone to form a separate pre-mix before manufacture.

Emollients useful in this invention (also denominated as "emollient component" here to include a single emollient as well as a mixture of emollients) may be selected from the group consisting of emollient oils such as a liquid mixture of hydrocarbons which are liquids at ambient temperatures (such as petroleum distillates and light mineral oils), mineral oil, peanut oil, sesame oil, avocado oil, coconut oil, cocoa butter, almond oil, safflower oil, corn oil, cotton seed oil, castor oil, olive oil, jojoba oil, paraffin oil, cod liver oil, palm oil, soybean oil, wheat germ oil, linseed oil, and sunflower seed oil; fatty acid esters such as isopropyl myristate, isopropyl palmitate, isopropyl stearate, isopropyl isostearate, butylstearate, octyl stearate, hexyl laurate, cetyl stearate, diisopropyl adipate, isodecyl oleate, diisopropyl sebacate, isostearyl lactate and lauryl lactate; fatty acids such as lauric, myristic, palmitic, stearic, oleic, linoleic, and behenic, acid; fatty alcohols such as lauryl, myristyl, cetyl, isocetyl, stearyl, isostearyl, oleyl, ricinoleyl, erucyl, and 2-octyl dodecanol, alcohols; lanolin and its derivatives such as lanolin, lanolin oil, lanolin wax, lanolin alcohols, lanolin fatty acids, isopropyl lanolate, ethoxylated lanolin, and acetylated lanolin alcohols such as ACETULAN®, a trademark and product of Amerchol Corporation, Edison, N.J.; selected silicones such as phenyl trimethicone and dimethicone copolyol wax (for example Dow Corning DC 2501, from Dow Corning Corporation, Midland, Mich.); and hydrocarbons such as petrolatum and squalene.

Particular emollients or emollient component may be selected to reduce wetness. Such emollients may be used to replace all or part of the normally used polyalkylene glycol monobutyl ether. These additional emollients include one or more members from the group consisting of diisopropyl adipate (also known as bis (1 -methylethyl) hexanedioate); dimethicone copolyol wax (for example Dow Corning DC 2501, from Dow Corning Corporation, Midland, Mich.); tetradecyl 2,2-dimethyl propanoate (also called myristyl neopentanoate (for example, DERMOL 145 from Alzo International Inc., Sayreville, N.J.); polyoxypropylene-3-myristyl ether (Promyristyl PM3); polyalkylene glycol monobutyl ether (UCON lubricant 50 HB 100); and (bis(1 -methylethyl) hexanedioate (DERMOL DIA). A particular combination of emollients includes polyoxypropylene-3-myristyl ether (Promyristyl PM3); polyalkylene glycol monobutyl ether (UCON lubricant 50 HB 100); and (bis(1 -methylethyl) hexanedioate (DERMOL DIA). These emollients may be used in amounts of 0.1–5% to give a total emollient (also referred to as emollient component) addition level of 0.5–10% (total emollient being the polyalkylene glycol monobutyl ether and this additional emollient component, which itself may be one or more of the additional emollients listed here).

A desired feature of the present invention is that a clear, transparent, or translucent composition, (for example, a clear or transparent deodorant or antiperspirant composition) can be provided. The term clear or transparent according to the present invention is intended to connote its usual dictionary definition; thus, a clear, for example, stick or gel antiperspirant composition of the present invention allows ready viewing of objects behind it. By contrast, a translucent composition, although allowing light to pass through, causes the light to be scattered so that it will be impossible to see clearly objects behind the translucent composition. An opaque composition does not allow light to pass through. Within the context of the present invention, a gel or stick is deemed to be transparent or clear if the maximum transmittance of light of any wavelength in the range 400–800 nm through a sample 1 cm thick is at least 35%, preferably at least 50%. The gel or stick is deemed translucent if the maximum transmittance of such light through the sample is between 2% and less than 35%. A gel or stick is deemed opaque if the maximum transmittance of light is less than 2%. The transmittance can be measured by placing a sample of the aforementioned thickness into a light beam of a spectrophotometer whose working range includes the visible spectrum, such as a Bausch & Lomb Spectronic 88 Spectrophotometer. As to this definition of clear, see European Patent Application No. 291 334 A2. Thus, according to the present invention, there are differences between transparent (clear), translucent and opaque compositions.

Particular embodiments of the invention which may be used are antiperspirant sticks having formulations which are at least translucent.

Because of the chemical instability of DBS in the presence of water in low pH media, it is preferred that antiperspirant formulations be essentially anhydrous and contain sufficient buffering agents to keep the pH in the range of 4.0–5.0. Deodorants and other cosmetic preparations which are at a higher pH do not require this restriction.

Throughout the present specification, where compositions are described as including or comprising specific components or materials, or where methods are described as including or comprising specific steps, it is contemplated by the inventors that the compositions of the present invention also consist essentially of, or consist of, the recited components or materials, and also consist essentially of, or consist of, the recited steps. Accordingly, throughout the present disclosure any described composition of the present invention can consist essentially of, or consist of, the recited components or materials, and any described method of the present invention can consist essentially of, or consist of, the recited steps.

As noted above, the compositions of the present invention have less tack than conventional cosmetic sticks especially since heretofore it has not been possible to incorporate silicone elastomers in cyclomethicone and DBS in the same formulation. This is especially true of antiperspirant sticks made according to the invention. Tack can be evaluated by various techniques. For the compositions of this invention, an in-house evaluation was done by applying product in the underarm area and comparing the tack to commercial products containing DBS. It was found that the products made according to this invention exhibited superior aesthetics compared to current products containing DBS. In the absence of the silicone elastomer these superior aesthetics will be reduced even in the presence of dimethicones.

Particular embodiments of the invention include:

FIRST EMBODIMENT

An anhydrous antiperspirant and/or deodorant comprising: (a) a solvent phase comprising: (i) 0.2–4.0 weight % dibenzylidene sorbitol (for example, 1.5–4.0% if a stick is made and 0.2–1% if a gel is made); (ii) 0.05–1.0 weight % of a co-gellant selected from the group consisting of hydroxyethylcellulose, hydroxypropyl cellulose, methylcellulose, and hydroxypropylmethylcellulose, especially hydroxypropyl cellulose; (iii) 25–75 weight % of a solvent selected from the group consisting of polyhydric alcohols for example, propylene glycol, dipropylene glycol, tripropylene glycol and tetrapropylene glycol, PPG-10 butane diol, 1,3-butane diol, PEG-6, PPG-425, 2-methyl-1, 3-propane diol ("MP Diol") and mixtures thereof, optionally including up to 50 percent of other solvents selected from the group consisting of propylene carbonate, diisopropyl sebacate, methyl pyrrolidone, and ethyl alcohol as a substitute for a portion of the polyhydric alcohol; (iv) an effective amount of at an antiperspirant or deodorant; and (v) 0.1–5 weight % dimethicone copolyol; and (b) an oil phase comprising: (i) 0.25–5 weight % of a silicone elastomer (on a solids basis) in a first dimethicone (for example, 1–20% elastomer in dimethicone at a concentration of 25% elastomer or its equivalent, wherein the dimethicone has a viscosity in the range of 6–100 centistokes (particularly 6–50 centistokes, and especially about 6 centistokes) and a flashpoint in the range of about greater than 115 degrees C. to 300 degrees C.; and (ii) 1–25 weight % of a second dimethicone (including the dimethicone from part (b)(i)) which may or may not be selected from the same group as the first dimethicone (preferably the second dimethicone is of the type described in part (b)(i) particularly having a viscosity in the range of 6–100 centistokes (such as 6–50 centistokes, and especially about 6 centistokes)); wherein the composition comprises less than 5 weight % water.

SECOND EMBODIMENT

An anhydrous antiperspirant and/or deodorant comprising: (a) a solvent phase comprising: (i) 0.2–4.0 weight % dibenzylidene sorbitol (for example, 1.5–4.0% if a stick is made and 0.2–1% if a gel is made); (ii) 0.05–1.0 weight % of a co-gellant selected from the group consisting of hydroxyethylcellulose, hydroxypropyl cellulose, methylcellulose, and hydroxypropylmethylcellulose, especially hydroxypropyl cellulose; (iii) 25–75 weight % of a solvent selected from the group consisting of polyhydric alcohols for example, propylene glycol, dipropylene glycol, tripropylene glycol and tetrapropylene glycol, PPG-10 butane diol, 1,3-butane diol, PEG-6, PPG-425, 2-methyl-1, 3-propane diol (MP Diol) and mixtures thereof, optionally including up to 50 percent of other solvents selected from the group consisting of propylene carbonate, diisopropyl sebacate, methyl pyrrolidone, and ethyl alcohol as a substitute for a portion of the polyhydric alcohol; (iv) an effective amount of at an antiperspirant or deodorant; and (v) 0.1–5 weight % dimethicone copolyol; and (b) an oil phase comprising:(i) 0.25–5 weight % of a silicone elastomer (on a solids basis) in a first dimethicone (for example, 1–20% elastomer in dimethicone at a concentration of 25% elastomer or its equivalent, wherein the dimethicone has a viscosity in the range of 6–100 centistokes (particularly 6–50 centistokes, and especially about 6 centistokes) and a flashpoint in the range of about greater than 115 degrees C. to 300 degrees C.: and (ii) 1–25 weight % of a second dimethicone (including the dimethicone from part (b)(i)) which may or may not be selected from the same group as the first dimethicone (preferably the second dimethicone is of the type described in part (b) (i) particularly having a viscosity in the range of 6–100 centistokes (such as 6–50 centistokes, and especially about 6 centistokes)); and (iii) 0–10 weight % of an emollient selected from the group consisting of phenyl trimethicone (especially 0.1–5 weight %); wherein the composition comprises less than 5 weight % water.

THIRD EMBODIMENT

An anhydrous antiperspirant and/or deodorant which is a stick product comprising:(a) a solvent phase comprising: (i) 1.5–4.0 weight % dibenzylidene sorbitol; (ii) 0.05–1.0 weight % of a co-gellant selected from the group consisting of hydroxyethylcellulose, hydroxypropyl cellulose, methylcellulose, and hydroxypropylmethylcellulose, especially hydroxypropyl cellulose; (iii) 25–75 weight % of a solvent selected from the group consisting of polyhydric alcohols for example, propylene glycol, dipropylene glycol, tripropylene glycol and tetrapropylene glycol, PPG-10 butane diol, 1,3-butane diol, PEG-6, PPG-425, 2-methyl-1, 3-propane diol ("MP Diol") and mixtures thereof, optionally including up to 50 percent of other solvents selected from the group consisting of propylene carbonate, diisopropyl sebacate, methyl pyrrolidone, and ethyl alcohol as a substitute for a portion of the polyhydric alcohol; (iv) an effective amount of at an antiperspirant or deodorant; and (v) 0.1–5 weight % dimethicone copolyol; and (b) an oil phase comprising: (i) 0.25–5 weight % of a silicone elastomer (on a solids basis) in a first dimethicone (for example, 1–20% elastomer in dimethicone at a concentration of 25% elastomer or its equivalent, wherein the dimethicone has a viscosity in the range of 6–100 centistokes (particularly 6–50 centistokes, and especially about 6 centistokes) and a flashpoint in the range of about greater than 115 degrees C. to 300 degrees C.; and (ii) 1–25 weight % of a second dimethicone (including the dimethicone from part (b)(i)) which may or may not be selected from the same group as the first dimethicone (preferably the second dimethicone is of the type described in part (b)(i) particularly having a viscosity in the range of 6–100 centistokes (such as 6–50 centistokes, and especially about 6 centistokes)); and (iii) 0–5 weight % phenyl trimethicone; wherein the composition comprises less than 5 weight % water.

The following Examples are given as illustrative of the invention but other modifications may be made by those skilled in the art which are within the spirit and scope of the invention. Unless otherwise noted all amounts are in weight percents. All chemical symbols and scientific abbreviations have their usual and customary meanings and all temperatures are in degrees C. The aluminum zirconium tetrachlorohydrex glycine complex listed in the following examples is a solution comprising about 28% by weight actives in propylene glycol (such as Westchlor® A2Z 4105 from Westwood Chemical, Middletown, N.Y.). In addition about 2–8%, particularly 3–4% by weight zinc glycinate was added to the actives solution. It will also be appreciated by those skilled in the art that preheating of ingredients was done as needed to ensure good mixing.

EXAMPLE A

As a general procedure for making the products of this invention (conveniently made in 400 gram samples), the following procedure can be used. Propylene glycol is weighed out into a main container. Hydroxypropyl cellulose is weighed out and sprinkled into the main container with mixing at room temperature. Mixing is continued for 10 minutes with high speed stirring but no splashing. The DBS (MILLITHIX 925 from Milliken, Spartanburg, S.C.) is weighed out and gradually added to the mixture with mixing. Mixing is continued at room temperature for 10 minutes with high speed stirring but no splashing. The mixture is heated to a temperature of about 100 degrees C. with continued mixing and dimethicone copolyol (Dow Corning DC 2507, which has been preheated to melt it if needed) is then added to the mixture. The mixture is further heated to about 110–175 degrees C. with continued mixing until the solution is clear and bright. A solution of the cosmetically active ingredient (aluminum zirconium tetrachlorohydrex gly in propylene glycol, A2Z 4105from Westwood Chemical Co., Middletown, N.Y. (28% active in propylene glycol)) is weighed out separately and heated to about 80 degrees C. In a third separate container, the silicone elastomer (KSG- 16 silicone elastomer from Shin-Etsu), additional dimethicone fluid of 6 cst viscosity (DM Fluid A from Shin-Etsu), and phenyl trimethicone (DC 556 from Dow Corning Corp., Midland, Mich.) are combined and mixed with heating to about 90 degrees C. The oil phase with the elastomer mixture is added to the aqueous phase in the first container with continuous stirring and heated to a temperature of about 100–102 degrees C. The ZAG in propylene glycol at 80 degrees C. is then added with continuous stirring. The final temperature of the composition is about 92–94 degrees C. If fragrance is used it is added at this point to the mixture, and the entire mixture is quickly cooled to about 90–92 degrees C. The mixture is then quickly poured into suitable ovoid shaped containers having dimensions of about 3 cm (width at widest part of oval)×6 cm (length of base)×10 cm (height). In general, the oil phase (internal phase) is 5–50% of the composition and the gellant/solvent phase is 50–95% of the composition.

EXAMPLE B

The method of Example A may be used but two separate slurries of (1) hydroxpropyl cellulose, DC 2501 and propylene glycol and (2) DBS and propylene glycol are made before mixing.

EXAMPLES 1–4

The method described in Example A may be used to make compositions of the invention with the amounts of ingredients listed in TABLE A.

TABLE A

| Ingredient (weight %) | Ex. 1 | Ex. 2 | Ex. 3 | Ex. 4 |
|---|---|---|---|---|
| Dibenzylidene sorbitol | 1.86 | 1.86 | 1.86 | 1.86 |
| Propylene glycol | 40.79 | 30.79 | 30.79 | 30.79 |
| Hydroxypropyl cellulose | 0.35 | 0.35 | 0.35 | 0.35 |
| Dimethicone copolyol | 1.00 | 1.00 | 1.00 | 1.00 |
| Antiperspirant active (28% in propylene glycol) | 30.00 | 40.00 | 43.60 | 40.00 |
| Phenyl trimethicone | 5.00 | 5.00 | 5.00 | 5.00 |
| Silicone elastomer (KSG-16) (25% in dimethicone of 6 cst) | 10.00 | 10.00 | 10.00 | 20.00 |
| Additional dimethicone fluid (6 cst) | 10.00 | 10.00 | 6.40 | — |
| Fragrance | 1.00 | 1.00 | 1.00 | 1.00 |

EXAMPLES 5–7

The method described in Example A may be used to make compositions of the invention with the amounts of ingredients listed in TABLE B.

TABLE B

| Ingredient (weight %) | Ex. 4 | Ex. 5 | Ex. 6 |
|---|---|---|---|
| Dibenzylidene sorbitol | 1.86 | 1.00 | 2.50 |
| Propylene glycol | 35.79 | 31.65 | 30.15 |
| Hydroxypropyl cellulose | 0.35 | 0.35 | 0.35 |
| Dimethicone copolyol | 1.00 | 1.00 | 1.00 |
| Antiperspirant active (28% in propylene glycol) | 43.60 | 40.00 | 40.00 |
| Phenyl trimethicone | 5.00 | 5.00 | 5.00 |
| Silicone elastomer (KSG-16) (25% in dimethicone of 6 cst) | 5.00 | 10.00 | 10.00 |
| Additional dimethicone fluid (6 cst) | 6.40 | 10.00 | 10.00 |
| Fragrance | 1.00 | 1.00 | 1.00 |

What is claimed is:

1. An anhydrous antiperspirant and/or deodorant product comprising:
   (a) a solvent phase comprising:
      (i) 0.2–4.0 weight % dibenzylidene sorbitol;
      (ii) 0.05–1.0 weight % of a co-gellant selected from the group consisting of hydroxyethylcellulose, hydroxypropyl cellulose, methylcellulose, and hydroxypropylmethylcellulose, especially hydroxypropyl cellulose;
      (iii) 25–75 weight % of a solvent selected from the group consisting of polyhydric alcohols, optionally including up to 50 percent of other solvents selected from the group consisting of propylene carbonate, diisopropyl sebacate, methyl pyrrolidone, and ethyl alcohol as a substitute for a portion of the polyhydric alcohol;
      (iv) an effective amount of at an antiperspirant or deodorant; and
      (v) 0.1–5 weight % dimethicone copolyol; and
   (b) an oil phase comprising:
      (i) 0.25–5 weight % of a silicone elastomer (on a solids basis) in a first dimethicone wherein the first dimethicone has a viscosity in the range of 6–100 centistokes and a flashpoint in the range of about greater than 115 degrees C. to 300 degrees C.; and
      (ii) 1–25 weight % of a second dimethicone (including the dimethicone from part (b)(i)) wherein the second dimethicone may be selected from the same group or a different group than the first dimethicone; and
      (iii) 0–10 weight % of an emollient.

2. A product as claimed in claim 1 comprising: 1.5–4.0 weight % dibenzylidene sorbitol.

3. A product as claimed in claim 1 comprising: 0.2–1 weight % dibenzylidene sorbitol.

4. A product as claimed in claim 1 wherein the co-gellant is hydroxypropyl cellulose.

5. A product as claimed in claim 1 wherein the polyhydric alcohol is selected from the group consisting of propylene glycol, dipropylene glycol, tripropylene glycol and tetrapropylene glycol, PPG-10 butane diol, 1,3-butane diol, PEG-6, PPG-425, 2-methyl-1,3-propane diol, and mixtures thereof.

6. A product as claimed in claim 1 wherein the antiperspirant is an aluminum zirconium salt stabilized with glycine or zinc glycinate.

7. A product as claimed in claim 1 wherein the first dimethicone has a viscosity in the range of about 6–50 centistokes.

8. A product as claimed in claim 1 wherein the first dimethicone has a viscosity in the range of about 6 centistokes.

9. A product as claimed in claim 1 wherein the silicone elastomer is used as 1–20% elastomer in the first dimethicone at a concentration of 25% elastomer or an equivalent amount.

10. A product as claimed in claim 1 wherein the second dimethicone is selected from the same group as the first dimethicone.

11. A product as claimed in claim 1 comprising from 0.1–10 weight % of an emollient.

12. A product as claimed in claim 11 wherein the emollient is phenyl trimethicone.

13. An anhydrous antiperspirant and/or deodorant product made by combining:
   (a) a solvent phase made by combining:
      (i) 0.5–4.0 weight % dibenzylidene sorbitol;
      (ii) 0.05–1.0 weight % of a co-gellant selected from the group consisting of hydroxyethylcellulose, hydroxypropyl cellulose, methylcellulose, and hydroxypropylmethylcellulose, especially hydroxypropyl cellulose;
      (iii) 25–75 weight % of a solvent selected from the group consisting of polyhydric alcohols, optionally including up to 50 percent of other solvents selected from the group consisting of propylene carbonate, diisopropyl sebacate, methyl pyrrolidone, and ethyl alcohol as a substitute for a portion of the polyhydric alcohol;
      (iv) an effective amount of at an antiperspirant or deodorant; and
      (v) 0.1–5 weight % dimethicone copolyol; and
   (b) an oil phase made by combining:
      (i) 0.25–5 weight % of a silicone elastomer (on a solids basis) in a first dimethicone wherein the first dimethicone has a viscosity in the range of 6–100 centistokes and a flashpoint in the range of about greater than 115 degrees C. to 300 degrees C.; and
      (ii) 1–25 weight % of a second dimethicone (including the dimethicone from part (b) (i)) wherein the second dimethicone may be selected from the same group or a different group than that the first dimethicone; wherein the oil phase is 5–50% of the composition and the solvent phase is 50–95% of the composition.

* * * * *